United States Patent
Stopek

(10) Patent No.: US 8,263,105 B2
(45) Date of Patent: *Sep. 11, 2012

(54) BIOMATERIAL DRUG DELIVERY AND SURFACE MODIFICATION COMPOSITIONS

(75) Inventor: Joshua Stopek, Yalesville, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 502 days.

This patent is subject to a terminal disclaimer.

(21) Appl. No.: 12/477,629

(22) Filed: Jun. 3, 2009

(65) Prior Publication Data

US 2009/0239786 A1    Sep. 24, 2009

Related U.S. Application Data

(63) Continuation-in-part of application No. 11/292,172, filed on Dec. 1, 2005, now Pat. No. 7,850,982.

(60) Provisional application No. 60/632,429, filed on Dec. 1, 2004.

(51) Int. Cl.
*A61F 2/00* (2006.01)

(52) U.S. Cl. ........................................... 424/423

(58) Field of Classification Search .................. None
See application file for complete search history.

(56) References Cited

U.S. PATENT DOCUMENTS

| | | | |
|---|---|---|---|
| 4,047,533 A | 9/1977 | Perciaccante et al. | |
| 4,492,714 A * | 1/1985 | Cooper et al. | 426/602 |
| 5,330,768 A | 7/1994 | Park et al. | |
| 5,352,515 A | 10/1994 | Jarrett et al. | |
| 5,442,016 A | 8/1995 | Jarrett et al. | |
| 5,530,074 A | 6/1996 | Jarrett et al. | |
| 5,621,050 A | 4/1997 | Jarrett et al. | |
| 5,716,376 A | 2/1998 | Roby et al. | |
| 5,780,044 A | 7/1998 | Yewey et al. | |
| 6,143,037 A * | 11/2000 | Goldstein et al. | 424/422 |
| 6,177,094 B1 | 1/2001 | Jiang | |
| 6,228,954 B1 | 5/2001 | Kaplan et al. | |
| 6,805,876 B2 | 10/2004 | Leong et al. | |
| 6,991,804 B2 | 1/2006 | Helmus et al. | |
| 2003/0022242 A1 | 1/2003 | Anderson | |
| 2004/0052746 A1 * | 3/2004 | Tamareselvy et al. | 424/70.11 |
| 2004/0106987 A1 * | 6/2004 | Palasis et al. | 623/1.42 |
| 2004/0142037 A1 * | 7/2004 | Engelmayer et al. | 424/486 |

FOREIGN PATENT DOCUMENTS

| | | |
|---|---|---|
| EP | 0 562 613 A | 9/1993 |
| EP | 0 752 245 A | 1/1997 |

OTHER PUBLICATIONS

European Search Report for EP 05025635.3 date of completion is Apr. 6, 2006 (3 pages).
Ha J C et al.: "Poly(ethylene oxide)-poly(propylene oxide)-poly(ethyleneoxide) (Pluronic)/poly(sigma-caprolactone) (PCL) amphiphilic block copolymeric nanospheres-I Preparation and characterization" Journal of Controlled Release, Elsecier, Amsterdam, NL, vol. 62, No. 3, Dec. 6, 1999.
Li et al., Morphology and Levonorgestrel Release Behavior of Polycaprolactone/Poly(ethylene oxide)/Polyactide Tri-component Copolymeric Microspheres, Polymers for Advanced Technologies, 2003, 14, 239-244.

* cited by examiner

*Primary Examiner* — Paul Dickinson

(57) ABSTRACT

An antimicrobial coating is provided for use on textiles, medical devices, packaging materials, and the like.

18 Claims, No Drawings

BIOMATERIAL DRUG DELIVERY AND SURFACE MODIFICATION COMPOSITIONS

CROSS-REFERENCE TO RELATED APPLICATIONS

This application is a continuation-in-part of U.S. application Ser. No. 11/292,172 filed Dec. 1, 2005 now U.S. Pat. No. 7,850,982, which in turn, claims benefit of and priority to U.S. Provisional Patent Application No. 60/632,429 filed Dec. 1, 2004, and the entire disclosures of each of the above-identified applications are hereby incorporated by reference in their entirety.

TECHNICAL FIELD

The present disclosure is related to compositions which are particularly useful in the manufacture of medical devices such as sutures, mesh, staples, clips, anastomosis rings, bone plates and screws, matrices for the sustained and/or controlled release of pharmaceutically active ingredients, etc. In some embodiments, the compositions may be utilized as coatings for medical devices.

BACKGROUND OF RELATED ART

Synthetic absorbable multifilament sutures such as DEXON™, VICRYL®, and POLYSORB™, commercially available from Ethicon, Inc. (Somerville, N.J.), and United States Surgical Corporation (Norwalk, Conn.), are known in the industry.

Suture coatings for synthetic absorbable sutures containing are also known. See, for example, U.S. Pat. Nos. 4,624,256; 4,190,720; 4,582,052; 4,605,730; 4,700,704; 4,705,820; 4,788,979; 4,791,929; 4,994,074; 5,047,048; 5,100,433; 5,133,739; and 5,352,515.

One important feature of a suture coating is its ability to enhance the suture's handling characteristics, such as surgeon's throw, lubricity, knot run down and/or knot security. The ability of a coating to adhere to, and remain adhered to, a medical device such as a suture, is another important feature. Although commercially available surgical sutures such as POLYSORB™ have excellent handling characteristics, it would be advantageous to provide a coated suture exhibiting even better surgeon's throw, lubricity, knot run down, and/or knot security properties, as well as improved adherence to a suture.

SUMMARY

The present disclosure provides compositions which may be utilized to form medical devices or coatings for such devices. For example, in embodiments, a medical device of the present disclosure may include a coating including an emulsion including an oil phase including at least one bioabsorbable polymer in combination with at least one organic solvent, and an aqueous phase including at least one antimicrobial component such as antimicrobial proteins, peptides, fragments thereof, and combinations thereof.

In other embodiments, a medical device coating of the present disclosure may include an emulsion including an oil phase including at least one bioabsorbable polymer in combination with at least one organic solvent, at least one surfactant, and an aqueous phase including at least one antimicrobial component such as lactoferrin, lactoferricin, defensins, cathelicidin, histatins, cecropins, magainin, and combinations thereof.

DETAILED DESCRIPTION

The present disclosure provides coatings suitable for medical devices, including sutures. In embodiments, a coating of the present disclosure may be applied as an emulsion, with the coating containing a medicinal agent, in embodiments an antimicrobial agent. The resulting coating may have improved adherence to a suture and improved antimicrobial properties compared with a coating applied as a solution.

Any polymer suitable for use as a coating may be utilized as a coating in accordance with the present disclosure. Polymers may be bioabsorbable or nonabsorbable. In embodiments, a bioabsorbable polymer may be utilized in forming a coating of the present disclosure. Bioabsorbable polymers which may be utilized as the coating include, for example, those polymers containing linkages derived from one or more monomers including glycolide, lactide, glycolic acid, lactic acid, caprolactone, trimethylene carbonate, dioxanones, dioxepanones, and the like, and homopolymers, copolymers and combinations thereof.

In embodiments, suitable materials which may be utilized in an emulsion to form the coatings of the present disclosure include homopolymers, copolymers, and/or blends possessing glycolic acid, lactic acid, glycolide, lactide, dioxanone, trimethylene carbonate, caprolactone, alkylene oxides such as polyethylene glycol (PEG), propropylene glycol (PPG), PEG/PPG copolymers, and various combinations of the foregoing.

For example, in embodiments, the polymeric material utilized to form the coating may include a caprolactone containing copolymer as described in U.S. Pat. No. 5,716,376, the entire disclosure of which is incorporated by reference herein. Such a caprolactone containing copolymer can be obtained by polymerizing a major amount of epsilon-caprolactone and a minor amount of at least one other copolymerizable monomer or mixture of such monomers in the presence of a polyhydric alcohol initiator.

Monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including alpha hydroxy acids (such as glycolic acid and lactic acid) and beta hydroxyacids (such as beta hydroxybutyric acid and gamma hydroxyvaleric acid); polyalkyl ethers (such as polyethylene glycol) and combinations thereof. In embodiments, glycolide can be utilized as the comonomer with epsilon-caprolactone in the bioabsorbable polymer.

Suitable polyhydric alcohol initiators which may be utilized in preparing a bioabsorbable polymer utilized as a coating include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being utilized in some embodiments.

The polyhydric alcohol initiator can be generally employed in small amounts, that is, from about 0.01 to about 5 weight percent of the total monomer mixture, in embodiments from about 0.1 to about 3 weight percent of the total monomer mixture.

The resulting bioabsorbable copolymer utilized as the coating can contain from about 70 to about 98 weight percent epsilon-caprolactone derived units, in embodiments from about 80 to about 95 weight percent epsilon-caprolactone derived units, the balance of the copolymer being derived from the other copolymerizable monomer(s), such as glycolide. In some embodiments, a caprolactone/glycolide copolymer at a ratio of about 90/10 weight percent may be utilized as the bioabsorbable polymer suitable for forming a coating in accordance with the present disclosure.

In other embodiments, the bioabsorbable polymer utilized as a coating may be a copolymer of lactide and glycolide. The amount of lactide in the copolymer may be from about 50% to about 90% by weight, in embodiments from about 60% to about 80% by weight, while the amount of glycolide in the copolymer may be from about 10% to about 50% by weight, in embodiments from about 20% to about 40% by weight. In some embodiments, a lactide/glycolide copolymer at a ratio of about 70/30 weight percent may be utilized as the bioabsorbable polymer.

In other embodiments, a copolymer of glycolide and trimethylene carbonate may be utilized in an emulsion to form a coating of the present disclosure. Methods for forming such copolymers are within the purview of those skilled in the art and include, for example, the methods disclosed in U.S. Pat. No. 4,300,565, the entire disclosure of which is incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments from about 30% to about 35% by weight of the copolymer.

Other suitable materials for forming an emulsion useful in forming coatings of the present disclosure include, in embodiments, copolymers of glycolide, dioxanone and trimethylene carbonate. Such materials may include, for example, copolymers possessing glycolide in amounts from about 55% to about 65% by weight of the copolymer, in embodiments from about 58% to about 62% by weight of the copolymer, in some embodiments about 60% by weight of the copolymer; dioxanone in amounts from about 10% to about 18% by weight of the copolymer, in embodiments from about 12% to about 16% by weight of the copolymer, in some embodiments about 14% by weight of the copolymer; and trimethylene carbonate in amounts from about 17% to about 35% by weight of the copolymer, in embodiments from about 22% to about 30% by weight of the copolymer, in embodiments about 26% by weight of the copolymer.

In other embodiments, a copolymer of glycolide, lactide, trimethylene carbonate and $\epsilon$-caprolactone may be utilized to form a coating of the present disclosure. Such materials may include, for example, a random copolymer possessing caprolactone in amounts from about 14% to about 20% by weight of the copolymer, in embodiments from about 16% to about 18% by weight of the copolymer, in some embodiments about 17% by weight of the copolymer; lactide in amounts from about 4% to about 10% by weight of the copolymer, in embodiments from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in embodiments about 7% by weight of the copolymer; and glycolide in amounts from about 60% to about 78% by weight of the copolymer, in embodiments from about 66% to about 72% by weight of the copolymer, in embodiments about 69% by weight of the copolymer.

Methods for forming these copolymers are also within the purview of those skilled in the art. In embodiments, the individual monomers may be combined in the presence of an initiator, such as diethylene glycol, and a catalyst, such as stannous octoate. The materials may be combined for a suitable period of time from about 4 hours to about 8 hours, in embodiments from about 5 hours to about 7 hours, in other embodiments for about 6 hours. In some cases the mixture may be held under an inert atmosphere, such as under nitrogen gas. The mixture may then be heated to a temperature of from about 80° C. to about 120° C., in embodiments from about 90° C. to about 110° C., in some cases to about 100° C., for a suitable period of time of from about 5 minutes to about 30 minutes, in embodiments from about 10 minutes to about 20 minutes, in other embodiments for about 15 minutes. The reaction mixture may then be heated to a temperature of from about 130° C. to about 170° C., in embodiments from about 140° C. to about 160° C., in embodiments to about 150° C., for a suitable period of time of from about 5 minutes to about 30 minutes, in embodiments from about 10 minutes to about 20 minutes, in other embodiments for about 15 minutes. The mixture may then be heated to a temperature of from about 170° C. to about 190° C., in embodiments to about 180° C., and allowed to polymerize for a period of from about 14 hours to about 24 hours, in embodiments from about 16 hours to about 20 hours, in some embodiments about 18 hours.

Any combination of the foregoing polymers may also be utilized to form a coating of the present disclosure.

In yet other embodiments, the polymeric material utilized to form a coating of the present disclosure may be a blend or emulsion of a first component made at least in part from a polyoxyalkylene copolymer, and a second component which may be a bioabsorbable polymer, oligomer, or copolymer, including those bioabsorbable polymers and copolymers described above.

For example, the first component can be a polymer made at least in part from a polyoxyalkylene block copolymer. Suitable polyoxyalkylene block copolymers include those having an A-B or A-B-A structure wherein "A" is a block made from repeating units of the formula—$O(CH_2)_n$—where n is from 1 to 4 and "B" is a block made from repeating units that are different from the repeating units in the A block and are selected from groups of the formula—$O(CH_2)_n$—where n is from 1 to 4. In particularly useful embodiments, a co-polymer designated as "PEO-PPO-PEO", wherein "PEO" denotes a block of repeating units of the formula—$OCH_2CH_2$—and "PPO" denotes a block of repeating units of the formula—$OCH_2CH_2CH_2$—. Particularly useful are triblock copolymers of the formula $HO(C_2H_4O)_a(C_3H_6O)_b(C_2H_4O)_cH$, wherein a and c are independently from about 1 to about 150 units, and b is from about 10 to about 200 units, with the overall molecular weight of from 1,000 to 50,000 daltons. Such polyoxyalkylene block copolymers are typically referred to by those skilled in the art as "poloxamers". In embodiments, useful poloxamers include those where a equals c and b is from about 10 to about 200 units.

Examples of polyoxyalkylene block copolymers which may be utilized to form the first component of a coating composition of the present disclosure include poloxamers sold under the trade names PLURONIC® (BASF Corp.) or SYNPERONIC® (ICI). PLURONIC® copolymers are identified by a specific letter-number combination. The alphabetical designation describes the physical form of the product: 'L' for liquids, 'P' for pastes, 'F' for solid forms. The first digit (two digits in a three-digit number) in the numerical designation, multiplied by 300, indicates the approximate molecular weight of the hydrophobic component (propylene oxide). The last digit, when multiplied by 10, indicates the approximate hydrophilic (ethylene oxide) content of the molecule as a percentage by weight. Thus, for example, PLURONIC® F68 is a solid material. The molecular weight of the hydrophobic (propylene oxide) component is approximately 1800 (6×300). The hydrophilic (ethylene oxide) component represents approximately 80% of the molecule by weight (8×10).

Poloxamers can be roughly divided into 3 main categories, all of which can be useful in making the first polymer component of the blends of the present disclosure, namely emulsion forming, micelle forming, and water soluble poloxamers. Various factors which determine poloxamer characteristics and behavior are the molecular weight, PPO:PEO ratio, temperature conditions, concentration, and presence of ionic materials. There is thus a wide range of characteristics in existing commercially available poloxamers which can be exploited in formulating the compositions of the present disclosure, especially where the composition further includes a medicinal agent and is utilized for drug delivery purposes.

In one embodiment, a suitable poloxamer which may be utilized to form the first polymeric component of a coating composition of the present disclosure includes a polyoxyethylene-polyoxypropylene triblock copolymer known as poloxamer 188, sold under the trade name PLURONIC® F68 by BASF (Parsippany, N.J.). Other poloxamers which may be utilized in the compositions of the present disclosure include poloxamer 403 (sold as PLURONIC® P123), poloxamer 407 (sold as PLURONIC® P127), poloxamer 402 (sold as PLURONIC® P122), poloxamer 181 (sold as PLURONIC® L61), poloxamer 401 (sold as PLURONIC® L121), poloxamer 185 (sold as PLURONIC® P65), and poloxamer 338 (sold as PLURONIC® F108).

The polyoxyalkylene block copolymers may, in some particularly useful embodiments, be reacted with additional biocompatible, biodegradable monomers to form the first polymeric component. Suitable monomers which may be reacted with the polyoxyalkylene block copolymers include, for example, alpha-hydroxy acids, lactones, carbonates, esteramides, anhydrides, amino acids, orthoesters, alkylene alkylates, alkylene oxides, biodegradable urethanes, and combinations thereof. Specific examples of suitable biocompatible, biodegradable monomers which may be added to the poloxamer include glycolide, lactide, hydroxybutyric acid, hydroxyvaleric acid, caprolactone, trimethylene carbonate, dimethyl trimethylene carbonate, p-dioxanone, and combinations thereof. These monomers, alone or in combination, can constitute up to about 90% to by total weight of the first polymeric component, in embodiments from about 10% to about 75% by total weight of the first polymeric component, in other embodiments from about 30% to about 65% by total weight of the first polymeric component, with the polyoxyalkylene block copolymer making up the balance of the first polymeric component. It should, of course, be understood that the other monomers may be reacted first to form a polymer (homopolymer or copolymer (e.g., random, block or the like)) prior to reaction with the polyoxyalkylene block copolymer. Conditions suitable for conducting such reactions are within the purview of one skilled in the art.

In some embodiments, in addition to a polyoxyalkylene block copolymer component, the first biocompatible polymeric component is made at least in part from epsilon-caprolactone, alone or in combination with other monomers. In one such embodiment, a polyoxyalkylene block copolymer is reacted with a epsilon-caprolactone polymer containing a major amount of epsilon-caprolactone and a minor amount of at least one other copolymerizable monomer or mixture of such monomers. In another embodiment, a polyoxyalkylene block copolymer is reacted with a monomer mixture that includes a major amount of epsilon-caprolactone and a minor amount of at least one other copolymerizable monomer or mixture of such monomers in the presence of a polyhydric alcohol initiator as disclosed in U.S. Pat. No. 6,177,094. The polymerization of these monomers contemplates all of the various types of monomer addition, i.e., simultaneous, sequential, simultaneous followed by sequential, sequential followed by simultaneous, etc. Suitable monomers which can be copolymerized with epsilon-caprolactone include glycolide, lactide, p-dioxanone and trimethylene carbonate.

In one embodiment, the first polymeric component includes a copolymer including from about 40% to about 95% (w/w) epsilon-caprolactone, from about 5% to about 15% (w/w) glycolide, and from about 5% to about 50% (w/w) poloxamer 188. In some embodiments, the first polymeric component utilized in forming the composition of the present disclosure may be a bioabsorbable terpolymer including about 51% epsilon-caprolactone, about 9% glycolide, and about 40% poloxamer 188, which is commercially available as POLYTRIBOLATE® (Tyco Healthcare, Mansfield, Mass.).

Methods for forming the first polymeric component, including a bioabsorbable terpolymer, are within the purview of those skilled in the art utilizing standard reaction conditions that may be varied depending upon the monomers and poloxamer utilized to form the first polymeric component. In some embodiments, the monomers and poloxamer can be combined in the presence of a catalyst such as stannous octoate, sometimes under an inert atmosphere, such as nitrogen gas. In other embodiments it may be desirable to allow the polymerization to occur under a vacuum, e.g., at a pressure less than about 1 Torr. In embodiments, the poloxamer, such as poloxamer 188, may be combined in a reaction vessel with additional monomers such as epsilon-caprolactone and glycolide in the presence of stannous octoate, heated to a suitable temperature of from about 170° C. to about 185° C., in embodiments from about 175° C. to about 180° C., such as about 178° C. The monomers may be allowed to polymerize for a suitable period of time which can be from about 4 hours to about 6 hours, in embodiments from about 4.25 hours to about 4.75 hours. After this time, the molten bioabsorbable polymeric component may be extruded. While not necessary, in some embodiments the bioabsorbable polymeric component may be subjected to a further heat treatment by heating to a temperature of from about 100° C. to about 120° C., in embodiments from about 107° C. to about 113° C., for a period of time of from about 25 hours to about 35 hours, in embodiments from about 28 hours to about 32 hours. In some cases it may be desirable for this second heat treatment to occur under a vacuum, at a pressure of less than about 1 Torr.

In some embodiments, the first polymeric component may be utilized alone in an effective antimicrobial amount to form a medical device or a coating for a substrate. An "effective antimicrobial amount" of a given component is an amount at which the component hinders the growth of bacteria associated with infections, and promotes the healing of a wound. Such coatings can prevent bacterial colonization on surfaces at levels of clinical infection, in some cases as much as 14 days or more.

However, the compositions of the present disclosure may include a first polymeric component including the copolymers described above, optionally in combination with a second polymer or oligomer. Suitable polymers and/or oligomers for use as the second component include the bioabsorbable polymers described above, including lactides, glycolides, lactide-co-glycolides, lactic acids, lactones, glycolic acids, carbonates, and the like, as well as dioxanones, esteramides, anhydrides, amino acids, orthoesters, dioxepanones, alkylene alkylates, alkylene oxides, absorbable urethanes, absorbable nylons, and homopolymers and copolymers thereof.

In some embodiments, the second component may be derived from two or more monomers, including polyethylene glycol-polypropylene glycol (PEG-PPG), polystyrene, n-vinyl pyrrolidine, n-vinyl pyridine, n-vinyl pyrrolidone, $C_1$-$C_{12}$ acrylate monomer, $C_1$-$C_{12}$ methacrylate monomer, hydroxyethyl methacrylate, hydroxypropyl methacrylate, acrylic acid, potassium sulfopropyl acrylate, potassium sulfopropyl methacrylate, and 2-methacryloyl phosphorylcholine. In some embodiments, the second component may be a copolymer of epsilon caprolactone and glycolide having approximately 85-95% (w/w) epsilon-caprolactone and 5-15% (w/w) glycolide.

In other embodiments, the second component may be a vinyl pyrrolidone component, including vinyl pyrrolidone homopolymers, vinyl pyrrolidone copolymers, and blends thereof optionally in combination with additional monomers or polymers described herein. Such copolymers may be of various molecular weights, for example, from about 10,000 g/mol to about 10,000,000 g/mol.

Where utilized, the amount of the first polymeric component made at least in part from a polyoxyalkylene copolymer may be present in compositions of the present disclosure in an amount of from about 2% by weight to about 100% by weight, in embodiments from about 5% by weight to about 80% by weight, in other embodiments from about 10% by weight to about 50% by weight of the bioabsorbable composition. The amount of second component in the blends or emulsions of the present disclosure may be up to about 98% by weight and, in embodiments, from about 20% by weight to about 95% by weight, in other embodiments from about 50% by weight to about 90% by weight of the composition of the present disclosure.

In some embodiments, the first polymeric component made at least in part from a polyoxyalkylene copolymer may be combined with the second component to form a blend. In other embodiments, the first polymeric component made at least in part from a polyoxyalkylene copolymer may be combined with the second component to form an emulsion or suspension.

In other embodiments, the polymeric components utilized to form the blend or emulsion of the present disclosure may be added separately to coat a substrate. In such a case, the substrate may be first coated with either of the components, i.e., the first polymeric component made at least in part from a polyoxyalkylene copolymer or the second component, followed by application of the other. Thus, in embodiments, the substrate may be first coated using a first composition containing a bioabsorbable polymer including epsilon-caprolactone, glycolide, and optionally a fatty acid component, such as a salt of a fatty acid ester (e.g., calcium stearoyl-2-lactylate). After the first coating has been applied, a second composition can be applied, such as a copolymer of epsilon-caprolactone, glycolide, and poloxamer 188, (e.g., the commercially available POLYTRIBOLATE® copolymer). Depending on the conditions of application, the two components can be applied as separate coatings or the two components can be sequentially applied and allowed to combine with each other on the surface of the substrate such as, for example, by controlling the rate of evaporation of the solvent.

In some embodiments, an emulsion used to form a coating of the present disclosure may also include a fatty acid component that contains a fatty acid, a fatty acid salt, or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to about 22 carbon atoms, and combinations thereof. Fatty acid salts including the calcium, magnesium, barium, aluminum, and zinc salts of stearic, palmitic and oleic acids may be useful in some embodiments of the present disclosure. Other salts which my be useful include commercial "food grade" calcium stearate which contains a mixture of about one-third $C_{16}$ and two-thirds $C_{18}$ fatty acids, with small amounts of the $C_{14}$ and $C_{22}$ fatty acids.

Suitable salts of fatty acid esters which may be included in the emulsion utilized to form a coating in accordance with the present disclosure include calcium, magnesium, aluminum, barium, or zinc stearoyl lactylate; calcium, magnesium, aluminum, barium, or zinc palmityl lactylate; and/or calcium, magnesium, aluminum, barium, or zinc olelyl lactylate. In embodiments, calcium stearoyl-2-lactylate (such as the calcium stearoyl-2-lactylate commercially available under the tradename VERV from American Ingredients Co., Kansas City, Mo.) may be utilized. Other fatty acid ester salts which may be utilized include lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

Where utilized, the amount of fatty acid component in the coating can be from about 5 percent to about 50 percent by weight of the total composition utilized to form the coating. In embodiments, the fatty acid component may be present in an amount from about 10 percent to about 20 percent by weight of the total composition utilized to form the coating.

In some embodiments it may be desirable to include a wax in the composition of the present disclosure. Suitable waxes which may be utilized include polyethylene wax, ethylene copolymer wax, halogenated hydrocarbon waxes, hydrogenated vegetable oil, beeswax, caranuba wax, paraffin, microcrystalline wax, candelillia, spermacetic wax, and mixtures thereof.

In other embodiments, omega-6 fatty acids, including arachidonic acid, may be added to the compositions of the present disclosure.

In yet additional embodiments, phospholipids may be added to the compositions of the present disclosure. Suitable phospholipids include, but are not limited to, phosphatidylcholine (PC), mono-acyl phosphatidylcholine (MAPC), diacyl phosphatidylcholine (DAPC), phosphatidylserine (PS), phosphatidylethanolamine (PE), phosphatidylinositol (PI), phosphatidylglycerol (PG), plasmalogen, sphingomyelin, ceramide, ciliatin, polymers having phospholipid groups, and derivatives thereof. In some embodiments copolymers having phosphorylcholine groups may be added to the compositions of the present disclosure, such as copolymers of 2-methacryloyloxyethyl phosphorylcholine with other monomers, including methacrylates such as butyl methacrylate, benzyl methacrylate, methacryloyloxyethyl phenylcarbamate, and phenyl methacryloyloxyethyl carbamate.

In embodiments, a polymer, such as the caprolactone/glycolide copolymer described above, can be present in an amount from about 45 to about 60 weight percent of the coating and the fatty acid component, such as a fatty acid salt or a salt of a fatty acid ester, can be present in an amount from about 40 to about 55 weight percent of the coating. In other embodiments, the polymer, such as the caprolactone/glycolide copolymer described above, can be present in an amount from about 50 to about 55 weight percent of the coating and the fatty acid component can be present in an amount from about 45 to about 50 weight percent of the coating.

In embodiments, a 52/48 weight percent mixture of glycolide/caprolactone polymer and calcium stearoyl lactylate can be utilized as the coating.

In some embodiments, the composition of the present disclosure may also include one or more medicinal agents which are released from the bioabsorbable blend in vivo. As used herein, "medicinal agent" is used in its broadest sense and includes any substance or mixture of substances that have clinical use. Consequently, medicinal agents may or may not have pharmacological activity per se, e.g., a dye. Examples of classes of medicinal agents which may be combined or mixed into the bioabsorbable blend of the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunosuppressants, gastrointestinal drugs, diuretics, steroids, polysaccharides, and enzymes. It is also intended that combinations of medicinal agents may be used.

Suitable antimicrobial agents which may be included as a medicinal agent in the bioabsorbable blend of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In embodiments, silver may be in particulate form, including microparticles and nanoparticles. In addition, polymer drugs, antimicrobial proteins and peptides such as lactoferrin and lactoferricin B, as well as combinations thereof, may be included as a medicinal agent in the blend or emulsion of the present disclosure. Lactoferrin and/or lactoferricin B may be obtained from animals such as goat, bovine, etc., human, or human recombinant sources. Other antimicrobials which may be included in a composition of the present disclosure include defensins, cathelicidin, histatins, cecropins, magainin, and combinations thereof.

Other medicinal agents which may be included as a medicinal agent in the composition of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antifungals; antivirals; anticoagulants; anticonvulsants; antidepressants; antihistamines; and immunological agents.

Other examples of suitable medicinal agents which may be included in the composition, such as a bioabsorbable blend or emulsion of the present disclosure, include viruses and cells, peptides (e.g., luteinizing-hormone-releasing-hormone analogues, such as goserelin and exendin) and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (.beta.-IFN, (.alpha.-IFN and .gamma.-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, gonadotropins (e.g., FSH, LH, CG, etc.), hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

The amount of medicinal agent present will depend upon the particular medicinal agent chosen, but typically the amount used will be in the range of 0.01 to 10% by weight of the composition.

In embodiments, the composition of the present disclosure may possess lactoferrin, lactoferricin, combinations thereof, and the like. Lactoferrin is a glycoprotein having a molecular weight of 80 kDa in milk and other body fluids, and plays an important role in the host defense system. Lactoferricin, as a peptide generated by hydrolysis of lactoferrin by the proteinase pepsin, has higher antimicrobial activity than lactoferrin.

Lactoferrin (LF) is a 80-kDa and lactoferricin (LFC) a pepsin hydrolysate of LF. Lactoferrin is an iron-binding glycoprotein found in milk of many species including human and cow. It is also present in exocrine fluids such as bile, saliva and tear. Both mammary epithelial and polymorphonulear cells can release this protein. Migration of leukocytes into milk during infection is accompanied by a spectacular increase of LF concentration in milk. The presence of LF in specific granules of neutrophils and its release in inflammatory reaction has been considered to play a role in immunomodulation. LF has also been shown to bound DNA, which can lead to the transcriptional activation of diverse molecules. Many reports identify LF as an important factor in host defense against infection and excessive inflammation. This protein in its iron-limited form, has been shown to inhibit the growth of many pathogenic microorganism. It was demonstrated the ability of LF to promote growth of *Bifidobacterium* spp. independently to its iron level. The binding of iron in the media is the most well-know mechanism by which LF induces growth inhibition of microorganism. LF-mediated bacteriostasis of Gram-negative microorganism may also involve its interaction with lipid A of lipopolysaccharide (LPS), and with pore forming proteins (porins) of the outer membrane altering integrity and permeability of microbial wall. It has been suggested that the binding of LF to the anionic lipoteichoic acid of *Staphylococcus epidermidis* decreased the negative charge allowing greater accessibility of lysozyme to the peptidoglycan. Other antimicrobial mechanisms of LF or LFC have not been described in Gram positive bovine mastitis pathogens.

The coatings of the present disclosure may contain other optional ingredients, such as stabilizing agents, thickeners, colorants, and the like. The optional ingredients may represent up to about 10% of the total weight of the coatings.

In embodiments, a suture in accordance with the present disclosure may be attached to any surgical needle within the purview of those skilled in the art to produce a needled suture. Wounds may be sutured by passing a needled suture through tissue to create wound closure. The needle may then be removed from the suture and the suture tied. The suture may remain in the tissue and help prevent contamination and infection of said tissue by virtue of its reduced bacterial colonization and/or its enhanced antimicrobial properties, thereby promoting wound healing and minimizing infection. The suture coating also advantageously enhances a surgeon's ability to pass the suture through tissue, and increases the ease and security with which the surgeon's can tie the suture.

The compositions of the present disclosure can be prepared using any technique within the purview of those skilled in the art. Where the polymers utilized to form the composition are both soluble in the same solvent, the appropriate amounts of each polymer can be dissolved in the solvent and applied to the medical device as a solution. Upon evaporation of the solvent, a coating of the blend will remain on the medical device. Some blends may be obtained with ordinary mixing. In other embodiments, especially where the bioabsorbable blend is to be utilized to deliver a medicinal agent, it may be desirable to mix the medicinal agent in the composition by processes such as ball mill, disc mill, sand mill, attritor, rotor stator mixer, ultrasonication, etc. In other embodiments, the two polymers can be melt blended and used to form or coat a medical device. Other methods for making and using the present blends will be readily apparent to those skilled in the art.

Alternatively, where the two components of the composition of the present disclosure are not completely miscible with each other or the solvents utilized to form the compositions, emulsions may be formed and utilized by any means known to those skilled in the art to form medical devices including drug delivery devices or coatings for medical devices.

When a medicinal agent is used, the medicinal agent may be placed in solution, the composition of the present disclosure may be placed in a separate solution, and the two combined to form an emulsion or suspension. Biocompatible dispersing agents in the form of surfactants, emulsifiers, or stabilizers may be added to the blend to assist in dispersion of the medicinal agent throughout the composition of the present disclosure.

Adjuvants may be added to stabilize or preserve the compositions described above. Such adjuvants include nonionic surfactants which include alcohol ethoxylates, glycerol esters, polyoxyethylene esters, glycol esters of fatty acids, and combinations thereof. Preferable nonionic surfactants are glycerol esters of stearic, oleic, and/or lauric acid, ethylene and/or diethylene glycol esters of fatty acids, and combinations thereof.

The compositions described herein are non-toxic. Depending on their particular physical and properties (to a large extent influenced by the nature of the polymers from which they are prepared), the blends and/or emulsions herein can be used in the fabrication in whole or in part of a variety of implantable medical devices and prostheses, e.g., clips, staples, sutures, suture coatings, etc. Applied to a suture, a coating composition containing the composition herein results in a suture having suitable lubricity, knot tiedown, and knot security characteristics.

Where the composition of the present disclosure is used to form a medical device, the devices may be made by injection molding the blend at temperatures and pressures known to those skilled in the art. Typically, the feed for the injection molding apparatus is a melt blend of the two polymer components in pellet form. The components should be quite dry when being injection molded in order to avoid hydrolytic degradation during processing. After molding, the surgical devices can be packaged and sterilized by conventional procedures. It may be desirable to anneal the devices to remove residual stresses and strains, to stabilize the shape of the device, and to reduce or eliminate defects in the piece. Annealing typically comprises reheating the medical device to above its glass transition temperature where chain mobility is greatest, and then slowly and gradually cooling the device to avoid reintroducing. Procedures, conditions and apparatus for annealing polymeric structures are well known in the art.

Where the composition of the present disclosure is used as an absorbable coating for a medical device, the coating may be formed using any known technique such as, for example, extrusion, molding and/or solvent casting. The composition can be used alone, blended with absorbable compositions, or blended with non-absorbable components. A wide variety of surgical articles can be coated with the compositions herein. These include, but are not limited to, clips and other fasteners, staples, sutures, pins, screws, prosthetic devices such as prosthetic tendons and prosthetic ligaments, wound dressings, drug delivery devices, woven mesh, lyophilized and biologic mesh, composite mesh, gauze, growth matrices, anastomosis rings, and other implantable devices. Fibers coated with the present compositions can be knitted or woven with other fibers, either absorbable or nonabsorbable to form meshes or fabrics.

In one embodiment the composition of the present disclosure may be applied as a coating by dissolving it in a solvent which is a non-solvent for any polymeric device to which the coating is to be applied. The solution containing the composition of the present disclosure may then be applied to a medical device by dipping the medical device into the solution, by passing the medical device past a brush or other applicator, or by spraying the solution onto the surface of the medical device. Suitable solvents for use in dissolving the composition of the present disclosure include, but are not limited to, volatile solvents such as methylene chloride and acetone. The medical device wetted with the coating solution may then be subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

Where applied in solution, the amount of solvent utilized can be from about 85% to about 99% by weight, in embodiments from about 90% to about 98% by weight of the solution utilized to apply the composition of the present disclosure, including the blend or emulsion described above, and any additional medicinal agents or adjuvants. In some embodiments the solvent may be present at about 95% by weight of the solution utilized to apply the composition of the present disclosure.

In other embodiments, the coating composition of the present disclosure may be applied as an emulsion. In embodiments, an emulsion may be prepared by: dissolving the first polymeric component in water, dissolving a second polymer in an organic solvent to thereby obtain the organic solution; contacting the organic solution and the aqueous solution to thereby obtain a mixture; and emulsifying the mixture to thereby obtain the emulsion.

The organic solvent may be chloroform, dichloromethane, carbon tetrachloride, methylene chloride, xylene, benzene, toluene, hexane, cyclohexane, diethyl ether, carbon disulfide, combinations thereof, and the like.

In embodiments, the ratio of the organic solution to the aqueous solution in the mixture may be from about 1 part organic solution to about 1 part aqueous solution, to from about 20 parts organic solution to about 1 part aqueous solution (i.e., from about 1:1 to about 20:1).

In other embodiments, the aqueous solution or the organic solution may contain the polymer component(s) of the coating, with the bioactive agent present in the other phase.

In embodiments, the coating compositions of the present disclosure include a water in oil (W/O) emulsion. While it is to be understood that any methods of preparing W/O emulsions are contemplated by the present disclosure, a W/O emulsion may be prepared by emulsifying an oil phase with an aqueous phase to yield an emulsion that appears milky.

For hydrophobic pharmaceutical agents, the oil phase may include at least one polymer and at least one hydrophobic pharmaceutical agent dissolved in an organic solvent that is immiscible with water. Thus, for hydrophobic pharmaceutical agents, coating compositions of the present disclosure may be prepared by dissolving at least one polymer and at least one pharmaceutical agent in a water-immiscible organic solvent to yield an oil phase and emulsifying the oil phase with an aqueous phase to yield a milky emulsion.

In another embodiment, the pharmaceutical agent is water-soluble or hydrophilic. For hydrophilic pharmaceutical agents, the oil phase may include at least one biodegradable biocompatible polymer dissolved in a water-immiscible organic solvent and the aqueous phase may include at least one water soluble or hydrophilic pharmaceutical agent dissolved in water.

Thus, for water-soluble or hydrophilic pharmaceutical agents, the coating compositions may be prepared by dissolving at least one biocompatible biodegradable polymer in a water-immiscible organic solvent to yield an oil phase, dissolving at least one water-soluble or hydrophilic pharmaceutical agent in water to yield an aqueous phase, and emulsifying the oil phase with the aqueous phase to yield a milky emulsion.

In other embodiments, the aqueous solution may include a bioactive agent, and the ratio of the organic solution to the aqueous solution in the mixture may be from about 3 parts organic solution to about 1 part aqueous solution, to from about 20 parts organic solution to about 1 part aqueous solution (i.e., from about 3:1 to about 20:1).

In other embodiments, the organic solution contains a hydrophobic bioactive agent, and the ratio of the organic solution to the aqueous solution in the mixture may be from about 1 part organic solution to about 1 part aqueous solution, to from about 8 parts organic solution to about 1 part aqueous solution (i.e., from about 1:1 to about 8:1).

The aqueous phase may further include other agents that enhance the stability of the pharmaceutical agent in water, as will be apparent to those having skill in the art. For example, the aqueous phase may further include pharmaceutically acceptable buffering agents for adjustment or maintenance of pH; salts; and the like.

Optionally, the aqueous phase may further include one or a plurality of emulsifying agents. Such agents may be useful to adjust the viscosity of the coating compositions, as will be discussed further below. When present, the emulsifying agent may be present in an amount of from about 0.1% to 10% (w/v) and in embodiments from about 1% to 3% (w/v) of the aqueous phase.

Suitable emulsifying agents include, by way of example and not limitation, fatty alcohols such as polyvinyl alcohol, lauryl alcohol, myristyl alcohol, cetyl alcohol, stearyl alcohol and oleyl alcohol; fatty acids such as lauric acid, myristic acid, palmitic acid, stearic acid, isostearic acid and oleic acid; fatty acid esters such as glycerol monostearate; polyoxyethylene sorbitan fatty acid esters sold commercially under the trademark TWEEN™ (registered trademarks of Hercules Inc., Wilmington, Del.; available from Sigma Chemical Co., St. Louis, Mo.); polyalkylene glycols such as polyethylene glycol; triethanolamine fatty acid esters such as triethanolamine oleate; fatty acid salts such as sodium oleate; sodium dodecyl sulfate (SDS); cellulose acetate; poloxamers such as block copolymers of ethylene oxide and propylene oxide sold under the trademarks PLURONIC F-68™ and PLURONIC F-127™ (registered trademarks of BASF; available from Sigma Chemical Co., St. Louis, Mo.); quaternary ammonium compounds such as didodecyldimethyl ammonium bromide (DMAB); and oils such as mineral oil, petrolatum, cottonseed oil, coconut oil, sesame seed oil, peanut oil, isopropyl myristate and isopropyl palmitate.

While the above description describes the use of a blend or emulsion as a medical device, drug delivery device, or coating composition in accordance with the present disclosure, optionally in combination with medicinal agents or adjuvants, similar methods and procedures may be utilized where the composition of the present disclosure includes coatings made at least in part from a single polymer in combination with a medicinal agent or adjuvant, without the addition of a second component, which can be a polymer or oligomer. As would be readily apparent to one skilled in the art, one could utilize the same or similar solvents, processing conditions, etc. in forming a composition of the present disclosure.

While the composition herein can be applied to any type of medical device, it may be especially useful as a coating for a suture. The amount of composition applied to a suture will vary depending upon the structure of the suture, e.g., monofilament or multifilament, the size of the suture and its composition. For multifilament sutures, the number of filaments and the tightness of the braid or twist may also influence the amount of coating.

The coating may be applied to both monofilament and multifilament braided sutures which may, in some embodiments, also be bioabsorbable. Suitable bioabsorbable monomers and polymers utilized for the sutures, including bioabsorbable braided sutures, include lactide, glycolide, trimethylcarbonate, epsilon-caprolactone, caprolactam, polyesters, nylons, etc. The coating can be present in an amount of from about 0.5 to about 15% (w/w) of the base suture substrate, in embodiments from about 1 to about 5% (w/w) of the base suture substrate. The thickness of the coating will depend on a number of factors, but can be from submicron thicknesses up to several millimeters in thickness.

The composition of the present disclosure, where utilized as a coating for a medical device, improves surface properties of the device such as, for example, cell and protein adhesion, lubricity, drug delivery, protein or DNA delivery, etc. The bioabsorbable blend coating may be especially useful in preventing bacterial adhesion/colonization, infection caused by or exacerbated by the device itself, and improving the handling properties of the device.

The composition of the present disclosure may also be formed into films and/or foams which, in turn, may be applied to wounds such as cuts, gashes, ulcers and burns to aid healing. Medicinal agents such as wound healing agents and antimicrobials may be incorporated to speed healing of damaged tissues. In this manner, various growth factors, antibiotics and antifungals can be incorporated into the bioabsorbable blend of the present disclosure.

Where medicinal agents are included in the bioabsorbable blend of the present disclosure, the composition of the present disclosure may be utilized as a drug delivery device to provide site-specific release of medicinal agents which may be immediate release, delayed release or sustained release. Immediate release systems provide a drug dose instantly. Delayed release systems provide repetitive intermittent dosings of drugs. Sustained release systems achieve slow release of a drug over an extended period of time and should maintain a therapeutically effective concentration of drug at the target site. Medicinal agents that are mingled with the compositions herein typically provide delayed or sustained release therapy by diffusion from the bioabsorbable implant and/or bioabsorbable coating as it degrades.

Any known technique may be employed for applying an emulsion to the article, in embodiments a suture. Suitable techniques include dipping, spraying, wiping and brushing. The article wetted with an emulsion may be subsequently passed through or held in a drying oven for a time and at a temperature sufficient to vaporize and drive off any liquid utilized in forming the emulsion.

Articles coated with coatings of the present disclosure may be formed from any material in need of improved resistance to bacteria. Such articles include, but are not limited to, textiles, packaging materials, medical devices, and the like.

Textiles which may be coated with coatings of the present disclosure include those made of natural fibers, synthetic fibers, blends of natural fibers, blends of synthetic fibers, and blends of natural fibers with synthetic fibers. Suitable materials utilized to form textiles include polyesters, polyamides, polyolefins, halogenated polymers, polyester/polyethers, polyurethanes, homopolymers thereof, copolymers thereof, and combinations thereof. Specific examples of suitable materials include polyethylene, polypropylene, polybutylene, polyvinyl chloride, polyethylene terephthalate, nylon 6, and nylon 6,6.

Medical devices which may be coated with a coating of the present disclosure include, but are not limited to, sutures, staples, meshes, patches, slings, stents, grafts, clips, pins, screws, rivets, tacks, bone plates, drug delivery devices, wound dressings, woven devices, non-woven devices, braided devices, adhesion barriers, tissue scaffolds, and other implants.

Medical devices can be formed from any material that has suitable physical properties for the intended use of the medical device. Medical devices can thus be formed of absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Suitable non-absorbable materials which may be utilized to form the medical device include polyolefins, such as polyethylene, polypropylene, copolymers of polyethylene and polypropylene, and blends of polyethylene and polypropylene.

In one embodiment, a medical device treated in accordance with the present disclosure may be a suture. Sutures in accordance with the present disclosure may be monofilament or multifilament and may be made of any conventional material, including both bioabsorbable and non-bioabsorbable materials, such as surgical gut, silk, cotton, polyolefins such as polypropylene, polyamides, polyglycolic acids, polyesters such as polyethylene terephthalate and glycolide-lactide copolymers, and the like.

In embodiments, the suture may be made of a polyolefin. Suitable polyolefins include polyethylene, polypropylene, copolymers of polyethylene and polypropylene, and blends of polyethylene and polypropylene. In some embodiments, polypropylene can be utilized to form the suture. The polypropylene can be isotactic polypropylene or a mixture of isotactic and syndiotactic or atactic polypropylene.

In other embodiments, the suture may be made from synthetic absorbable polymers such as those made from glycolide, lactide, caprolactone, alkylene carbonates (i.e., trimethylene carbonate, tetramethylene carbonate, etc.), dioxanones, and copolymers and combinations thereof. One combination which may be utilized includes glycolide and lactide based polyesters, including copolymers of glycolide and lactide.

As noted above, the suture can be monofilament or multifilament. Where the suture is a monofilament, methods for producing such sutures are within the purview of those skilled in the art. Such methods include forming a suture material, such as a polyolefin resin, and extruding, drawing and annealing the resin to form the monofilament.

Where the sutures are made of multiple filaments, the suture can be made using any technique within the purview of one skilled in the art such as, for example, braiding, weaving and/or knitting. The filaments may also be combined by fusing, adhering, gluing, coating, over extruding (sheath/core), and the like, to produce a non-woven suture. The filaments themselves may be drawn, oriented, crinkled, twisted, commingled or air entangled to form yarns as part of the suture forming process.

In embodiments a multifilament suture of the present disclosure can be produced by braiding. The braiding can be done by any method within the purview of those skilled in the art. For example, braid constructions for sutures and other medical devices are described in U.S. Pat. Nos. 5,019,093, 5,059,213, 5,133,738, 5,181,923, 5,226,912, 5,261,886, 5,306,289, 5,318,575, 5,370,031, 5,383,387, 5,662,682, 5,667,528, and 6,203,564, the entire disclosures of each of which are incorporated by reference herein. Once the suture is constructed, it can be sterilized by any means within the purview of those skilled in the art.

In some cases a tubular braid, or sheath, can be constructed about a core structure which is fed through the center of a braider. Known tubular braided sutures, including those possessing cores, are disclosed, e.g., in U.S. Pat. Nos. 3,187,752, 3,565,077, 4,014,973, 4,043,344, and 4,047,533.

A suture coated in accordance with the present disclosure may possess antimicrobial properties. A suture coated in the present disclosure may also resist bacterial colonization due, in part, to its smooth surface which is resistant to colonization. In embodiments, a suture of the present disclosure may possess an elongate structure and be formed from at least one polymeric filament, in embodiments multiple filaments. The filaments may be formed from a polymeric material that is absorbable under physiological conditions, and a coating of the present disclosure may be placed thereon.

Medical devices such as sutures and packaging materials in accordance with this disclosure can be sterilized in accordance with techniques within the purview of those skilled in the art. For example, medical devices such as sutures may be subjected to ethylene oxide treatments, gamma radiation, electron beam radiation, plasma treatments, combinations thereof, and the like, to sterilize the suture and any coating thereon.

Textiles, including individual fibers and fabrics made of multiple fibers, may be formed and/or coated in a similar manner.

Coatings of the present disclosure remain attached to the surface of the article during the processing, handling, and storage of the article. This minimizes the loss or transfer of the coating from an article to any packaging, from any packaging to any article, the environment, etc.

The following examples are illustrative of specific embodiments of the polymeric compositions and should not be construed as limitations thereof.

EXAMPLE 1

A biocompatible, biodegradable polymer was produced as follows. A one gallon reactor vessel was cleaned and subjected to a vacuum to reach a pressure of less than 1 Torr. 1000±1 grams of poloxamer 188 (PLURONIC® F68) was added to the one gallon reactor vessel, after which time a vacuum was again applied to obtain a pressure less than 1 Torr. The temperature was raised to about 105° C. and the PLURONIC® F68 was dried in the reactor for about 14 (±4) hours. During this time period, 1275±1 grams of epsilon-caprolactone was added to a 3 liter round bottom flask, and 225±1 grams of glycolide was added to a 500 ml round bottom flask. Between 75 and 90 minutes prior to the end of the drying of the PLURONIC® F68, the epsilon-caprolactone and glycolide were placed in an oven heated to a temperature of 105° C. After the drying of the PLURONIC® F68 was complete, the glycolide was added to the reactor, followed by the addition of the epsilon-caprolactone. The reactor was then backfilled with nitrogen, and then 295 μL of stannous octoate was added to the reactor as a catalyst.

The reactor was then heated to 178° C. (±3° C.), and the reaction was allowed to continue for 4.5 (±0.25) hours. After the reaction was complete, the polymerized bioabsorbable polymer was extruded and allowed to cool for a minimum of 16 hours.

The resulting bioabsorbable polymer was then subjected to an additional heat treatment. The bioabsorbable polymer was placed in a vacuum oven, which was heated to a temperature of 110° C. (±3° C.) in a vacuum at a pressure less than 1 Torr, for 30±2 hours. After heating, the polymer was allowed to cool under vacuum for a minimum of 6 hours.

NMR of the bioabsorbable polymer was conducted utilizing a Bruker AC300 NMR spectrometer. The proton spectra obtained had peaks which permitted the identification of the components of the bioabsorbable polymer.

The resulting bioabsorbable terpolymer was found to possess about 40% by weight PLURONIC® F68, about 51% by weight of caprolactoyl groups, about 9% by weight of glycoyl groups, and ≦1% by weight of residual caprolactone monomer.

EXAMPLE 2

Monofilament surgical sutures which prevented the attachment and colonization of bacteria and provided enhanced suture handling characteristics, including reduced tissue drag, were prepared as follows. The polymer of Example 1 was solvated in methylene chloride at concentrations of 2, 5 and 10% (w/w). Monofilament polybutester (a copolymer of butylene terephthalate and polytetramethylene ether glycol) surgical sutures were coated by dip coating with each solution, to produce a uniform coating on the sutures. The resulting coating levels were 1.08%, 3.64% and 6.80% based on the weight of the suture for the 2%, 5% and 10% solutions, respectively. The coating from the 10% solution was found to prevent bacterial colonization of sutures at levels of clinical infection for at least 8 days. In contrast, other monofilaments, including uncoated polybutester sutures reached levels of clinical infection in as little as 3 days.

EXAMPLE 3

Braided multifilaments made of a glycolide/lactide copolymer coated with a mixture of a caprolactone/glycolide copolymer and calcium stearoyl lactylate as described in the Examples of U.S. Pat. No. 5,716,376 (the disclosure of which is incorporated herein by this reference) were coated with the polymer of Example 1. The coating polymer was solvated in methylene chloride (2, 5 and 10% (w/w)) and the sutures coated with one of three solutions by dip coating. The additional coating polymer prevented bacterial adhesion and colonization in a more effective manner than observed with the uncoated sutures or with Ethicon's VICRYL® Plus suture (a suture made of a glycolide/lactide copolymer having a coating including triclosan).

EXAMPLE 4

This bioabsorbable polymer of Example 1 was blended with the solution of Example 3 of U.S. Pat. No. 5,716,376 containing an epsilon-caprolactone/glycolide copolymer and calcium stearoyl lactylate represented about 2, 5 and 10% (w/w) of the resulting solution.

Multifilament braided glycolide/lactide surgical sutures were coated with the bioabsorbable blend by dip coating the suture in the solution having the bioabsorbable blend, and driving off the solvent by heating to produce a useable surgical suture.

EXAMPLE 5

Antimicrobial surgical suture coatings containing ionic silver and/or silver glass particles are prepared as follows. The bioabsorbable polymer of Example 1 is solvated in methylene chloride at concentration of 10% (w/w). Suspension/solutions of various silver salts (nitrate, citrate, sulfadiazine, lactate, etc.) are prepared in reverse osmosis (RO) water under high speed mixing. Water/organic emulsions are prepared with the ratio of the bioabsorbable polymer coating solution: silver suspension/solutions ranging from 8:2 to 2:8. Emulsions are formed under vigorous stirring and surgical sutures were coated by dip coating techniques. The coating is present in an amount from 0.5% to 15% (w/w) of the base suture substrate, in embodiments from about 1% to about 5% (w/w). The polymer coating containing ionic silver prevents bacterial colonization on the suture material.

EXAMPLE 6

Commercially available uncoated POLYSORB™ sutures (USSC) were dip coated in a 1% (w/v) polyvinyl pyrrolidone aqueous solution (the PVP was from Aldrich) and dried at about 40° C. overnight under vacuum. Suture strands of about 5 cm in length were packaged and sterilized by ethylene oxide. Strands were assayed for anti-colorization properties as follows. Bacterial stocks of *E. coli* (from ATTC cultures) were prepared from a McFarland standard of Log 8 and diluted to a stock concentration of Log 3. Suture strands were placed in 15 ml glass centrifuge tubes and inoculated with Log 3 *E. coli* (about 10 ml) and incubated overnight at about 37° C. and under shear (by subjecting them to a rocking bath).

The strands were removed and sonicated for about 5 seconds in fresh tryptic soy broth (TSB), transferred to fresh TSB and vortexed for about 10 minutes to remove adherent bacteria. After the vortex step, about 1 ml of TSB was plated on nutrient agar and incubated overnight and counted for colony forming units (CFUs). The PVP coated POLYSORB exhibited a six log reduction compared to standard POLYSORB sutures.

EXAMPLE 7

A top coat of PVP was applied to POLYSORB sutures possessing a coating of a 52/48 weight percent mixture of a glycolide/caprolactone polymer and calcium stearoyl lactylate using either aqueous or organic solutions of PVP at concentrations of 1% and 2% (w/v) and (w/w), respectively. Coatings were prepared using a Deitz and Schell coating apparatus with a line speed of 40 meters/minute and heated in an oven at a temperature of approximately 100° C. The resulting sutures were dried overnight as described above in Example 1.

EXAMPLE 8

Blend coatings of PVP with a lactide/glycolide copolymer (about 70% by weight lactide and about 30% by weight glycolide), PVP with a glycolide/caprolactone copolymer (about 90% by weight caprolactone and about 10% by weight glycolide), and PVP with both copolymers, that is the 70/30 lactide/glycolide copolymer and the 90/10 caprolactone/glycolide copolymer, were dip coated as described above in Example 1. Stock solutions of the copolymers were prepared and PVP was added to achieve a range of final PVP solution concentrations of 0.1 to 5% (w/w). All solutions utilized methylene chloride as the solvent. These solutions were dip coated and dried as stated in Example 1. Some compositions were top coated with aqueous PVP solutions. Top coats included aqueous PVP (1% w/v (10 mg/ml)) in which a previously coated suture was over coated with aqueous PVP by immersion coating ($\leq$1 minute) to provide top barrier layer of PVP.

EXAMPLE 9

Combinations of high molecular weight PVP top coats layered over varied lower molecular weight PVP blend coatings, some of which are incorporated into hydrophobic polymers or blends thereof to extend the anti-colonization efficacy and duration by affording a longer PVP residence time on the suture when in a physiologic aqueous environment. A high molecular weight PVP may have a molecular weight of >900,000 g/mol, while a low molecular weight PVP may have a molecular weight of <100,000 g/mol. Hydrophobic polymers including the PVP may include silicone/PEG copolymers or blends.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A medical device coating comprising an emulsion comprising:
    an oil phase comprising a bioabsorbable terpolymer comprising from about 30 to about 50 weight percent of a polyoxyalkylene copolymer, from about 40 to about 50 weight percent epsilon-caprolactone, the balance of the copolymer comprising at least one other copolymerizable monomer selected from the group consisting of glycolide, lactide, p-dioxanone and trimethylene carbonate, in combination with a polymer comprising two or more monomers selected from the group consisting of lactide, glycolide, lactic-acid, lactones, glycolic acid, carbonates, orthoesters, absorbable urethanes, absorbable nylons, polyethylene glycol-polypropylene glycol, polystyrene, n-vinyl pyrrolidine, n-vinyl pyridine, $C_1$-$C_{12}$ acrylate monomer, $C_1$-$C_{12}$ methacrylate monomer, hydroxyethyl methacrylate, hydroxypropyl methacrylate, acrylic acid, potassium sulfopropyl acrylate, potassium sulfopropyl methacrylate, and 2-methacryloyl phosphorocholine, in combination with at least one organic solvent; and
    an aqueous phase comprising at least one antimicrobial component selected from the group consisting of antimicrobial proteins, peptides, fragments thereof, and combinations thereof.

2. The coating of claim 1, wherein the polymer comprises a lactide/glycolide copolymer.

3. The coating of claim 1, wherein the at least one antimicrobial component is selected from the group consisting of lactoferrin, lactoferricin, defensins, cathelicidin, histatins, cecropins, magainin, and combinations thereof.

4. The coating of claim 1 wherein coating further comprises a vinyl pyrrolidone component selected from the group consisting of vinyl pyrrolidone homopolymers, vinyl pyrrolidone copolymers, and blends thereof optionally in combination with additional monomers or polymers.

5. The coating of claim 1, wherein the coating further comprises one or more fatty acid components selected from the group consisting of fatty acids, fatty acid salts and salts of fatty acid esters.

6. The coating of claim 5, wherein the fatty acid component comprises a salt of a fatty acid ester selected from the group consisting of calcium stearoyl lactylate, magnesium stearoyl lactylate, aluminum stearoyl lactylate, barium stearoyl lactylate, zinc stearoyl lactylate calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, and zinc olelyl lactylate.

7. The coating of claim 1, wherein the medical device is selected from the group consisting staples, clips, drug delivery devices, stents, pins, screws, sutures, prosthetic ligaments, prosthetic tendons, woven mesh, tissue scaffolds, lyophilized and biologic mesh, composite mesh, gauze, dressings, and growth matrices.

8. The coating of claim 1, wherein the organic solvent is selected from the group consisting of chloroform, dichloromethane, carbon tetrachloride, xylene, benzene, toluene, hexane, cyclohexane, diethyl ether, carbon disulfide, and combinations thereof.

9. The coating of claim 1, wherein the ratio of the organic solution to the aqueous solution may be from about 1:1 to about 20:1.

10. A medical device coating comprising an emulsion comprising:
- an oil phase comprising a bioabsorbable terpolymer comprising from about 30 to about 50 weight percent of a polyoxyalkylene copolymer, from about 40 to about 50 weight percent epsilon-caprolactone, the balance of the copolymer comprising at least one other copolymerizable monomer selected from the group consisting of glycolide, lactide, p-dioxanone and trimethylene carbonate, in combination with a polymer comprising two or more monomers selected from the group consisting of lactide, glycolide, lactic-acid, lactones, glycolic acid, carbonates, orthoesters, absorbable urethanes, absorbable nylons, polyethylene glycol-polypropylene glycol, polystyrene, n-vinyl pyrrolidine, n-vinyl pyridine, $C_1$-$C_{12}$ acrylate monomer, $C_1$-$C_{12}$ methacrylate monomer, hydroxyethyl methacrylate, hydroxypropyl methacrylate, acrylic acid, potassium sulfopropyl acrylate, potassium sulfopropyl methacrylate, and 2-methacryloyl phosphorocholine, in combination with at least one organic solvent;
- at least one surfactant; and
- an aqueous phase comprising at least one antimicrobial component selected from the group consisting of lactoferrin, lactoferricin, defensins, cathelicidin, histatins, cecropins, magainin, and combinations thereof.

11. The coating of claim 10, wherein the polymer comprises a lactide/glycolide copolymer.

12. The coating of claim 10, wherein the at least one surfactant is selected from the group consisting of alcohol ethoxylates, glycerol esters, polyoxyethylene esters, glycol esters of fatty acids, and combinations thereof.

13. The coating of claim 10, wherein the coating further comprises a vinyl pyrrolidone component selected from the group consisting of vinyl pyrrolidone homopolymers, vinyl pyrrolidone copolymers, and blends thereof, optionally in combination with additional monomers or polymers.

14. The coating of claim 10, wherein the coating further comprises one or more fatty acid components selected from the group consisting of fatty acids, fatty acid salts and salts of fatty acid esters.

15. The coating of claim 14, wherein the fatty acid component comprises a salt of a fatty acid ester selected from the group consisting of calcium stearoyl lactylate, magnesium stearoyl lactylate, aluminum stearoyl lactylate, barium stearoyl lactylate, zinc stearoyl lactylate calcium palmityl lactylate, magnesium palmityl lactylate, aluminum palmityl lactylate, barium palmityl lactylate, or zinc palmityl lactylate, calcium olelyl lactylate, magnesium olelyl lactylate, aluminum olelyl lactylate, barium olelyl lactylate, and zinc olelyl lactylate.

16. The coating of claim 10, wherein the medical device is selected from the group consisting staples, clips, drug delivery devices, stents, pins, screws, sutures, prosthetic ligaments, prosthetic tendons, woven mesh, tissue scaffolds, lyophilized and biologic mesh, composite mesh, gauze, dressings, and growth matrices.

17. The coating of claim 10, wherein the organic solvent is selected from the group consisting of chloroform, dichloromethane, carbon tetrachloride, xylene, benzene, toluene, hexane, cyclohexane, diethyl ether, carbon disulfide, and combinations thereof.

18. The coating of claim 10, wherein the ratio of the organic solution to the aqueous solution may be from about 1:1 to about 20:1.

* * * * *